United States Patent
Kono et al.

(10) Patent No.: US 6,730,702 B1
(45) Date of Patent: May 4, 2004

(54) THERAPEUTIC AGENTS FOR INFLAMMATORY DISEASES OF INTESTINE

(75) Inventors: Toru Kono, Asahikawa (JP); Masafumi Nomura, Sapporo (JP)

(73) Assignee: Tanabe Seiyaku Co., Ltd., Osaka (JP)

(*) Notice: Subject to any disclaimer, the term of this patent is extended or adjusted under 35 U.S.C. 154(b) by 35 days.

(21) Appl. No.: 10/129,361

(22) PCT Filed: Nov. 9, 2000

(86) PCT No.: PCT/JP00/07855
§ 371 (c)(1),
(2), (4) Date: May 3, 2002

(87) PCT Pub. No.: WO01/34143
PCT Pub. Date: May 17, 2001

(30) Foreign Application Priority Data

Nov. 11, 1999 (JP) ............................. 11/321058
Jul. 26, 2000 (JP) ........................... 2000/225442

(51) Int. Cl.⁷ .................. A61K 31/19; A61K 27/00; A61K 31/495
(52) U.S. Cl. .................. 514/569; 514/553; 514/555
(58) Field of Search ............... 514/569, 553, 514/555

(56) References Cited

FOREIGN PATENT DOCUMENTS

| EP | 0078152 A1 | 5/1983 |
|---|---|---|
| JP | 5877814 A | 5/1983 |
| JP | 63165361 A | 7/1988 |
| JP | 2167258 A | 6/1990 |
| JP | 10338632 A | 12/1998 |

OTHER PUBLICATIONS

Ohkusa et al., "Disappearance of hyperplastic polyps in the stomach after eradication of Helicobacter pylori: A randomized, controlled trial", abstract, Annals of Internal Medicine, 1998, 129(9), 712–715.*

Ohkusa et al.. "Prosepective evaluation of a new anti–ulcer agent, ecabet sodium, for the treatment of Helicobacter pylori infection", abstract, Alimentary Pharmacology and Therapeutics, 1998, 12(5), 457–461.*

Yarimizu et al., *Oncology Reports,* vol. 5, pp. 1103–1107 (1998).

* cited by examiner

*Primary Examiner*—Zohreh Fay
*Assistant Examiner*—Brian-Yong S. Kwon
(74) *Attorney, Agent, or Firm*—Birch, Stewart, Kolasch & Birch, LLP

(57) ABSTRACT

The present invention provides a novel agent for prophylaxis or treatment of inflammatory bowel diseases for oral administration or intra-intestinal infusion, which comprises as an active ingredient a compound of the formula (I):

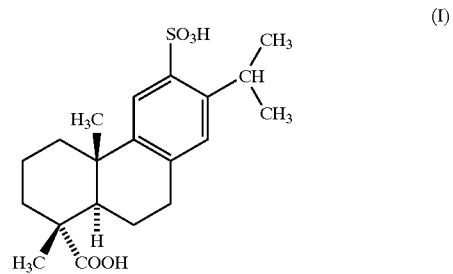

or a pharmaceutically acceptable salt thereof; a use of said active ingredient in preparation of an agent for prophylaxis or treatment of inflammatory bowel diseases; and a method for prophylaxis or treatment of inflammatory bowel diseases.

6 Claims, No Drawings

THERAPEUTIC AGENTS FOR INFLAMMATORY DISEASES OF INTESTINE

This application is the national phase under 35 U.S.C. §371 of PCT International Application No. PCT/JP00/07855 which has an International filing date of Nov. 9, 2000, which designated the United States of America.

TECHNICAL FIELD

The present invention relates to a novel agent for prophylaxis or treatment of inflammatory bowel diseases, more particularly an agent for prophylaxis or treatment of inflammatory bowel diseases which comprises as an active ingredient sulfodehydroabietic acid or a pharmaceutically acceptable salt thereof, and a use of said active ingredient in preparation of an agent for prophylaxis or treatment of inflammatory bowel diseases, and further relates to a method for prophylaxis or treatment of inflammatory bowel diseases.

BACKGROUND ART

Inflammatory bowel diseases include intractable inflammatory diseases of large and small intestines which are caused by various nosogenesis, for example, ulcerative colitis which is a cryptogenic diffuse non-specific inflammation wherein mucosa on the large intestine is mainly invaded and erosion and ulcer are formed, or Crohn's disease which is a cryptogenic non-specific granulomatous inflammatory disease accompanied by fibrosis or ulcer. In addition, the lesion of the intestine in Behçet's disease which is a chronic systemic inflammatory disease is also included.

The nosogenesis of ulcerative colitis, Crohn's disease, or Behçet's disease has not been clarified yet, but their immunological mechanisms have recently attracted a lot of attentions. In the medication of these inflammatory bowel diseases, immunosupressants, steroids, salazosulfapyridine, etc. have been used, but they cannot exhibit sufficient effects in certain patients. Besides, they should be improved with respect to side effects, and under these circumstances, it has been desired to develop a medicament being more effective and having a high safety.

On the other hand, sulfodehydroabietic acid or a salt thereof has been known to exhibit an inhibitory activity of acid secretion or pepsin secretion, etc., and to be useful as an agent for prophylaxis or treatment of peptic ulcer (gastric ulcer, duodenal ulcer) or gastritis (JP-A-58-77814, JP-A-63-165361, JP-A-2-167258). It is considered that peptic ulcer (gastric ulcer, duodenal ulcer) or gastritis and inflammatory bowel diseases are different in not only their lesion regions, but also their nosogenesis is quite different. In the nosogenesis of peptic ulcer such as gastric ulcer and duodenal ulcer, the digestion by gastric juice cannot be left out of consideration. In the medication of these diseases, a medicament exhibiting an inhibitory activity of acid secretion such as a histamine H2 receptor antagonist or a proton pump inhibitor is mainly used in the medication of peptic ulcer and gastritis. On the other hand, an immunosupressant, a steroid, a salazosulfapyridine, etc. is mainly employed in the medication of inflammatory bowel diseases, which is quite different from the medication of peptic ulcer or gastritis.

It has not been known at all that sulfodehydroabietic acid or a salt thereof is useful in the prophylaxis or treatment of inflammatory bowel diseases.

DISCLOSURE OF INVENTION

An object of the present invention is to provide a novel agent being useful in the prophylaxis or treatment of inflammatory bowel diseases.

During the studies on a novel remedy for inflammatory bowel diseases, the present inventors have found that sulfodehydroabietic acid disclosed in JP-A-58-77814, JP-A-63-165361, etc. or a pharmaceutically acceptable salt thereof exhibits an excellent effect in the prophylaxis or treatment of inflammatory bowel diseases, and have accomplished the present invention.

That is, the present invention provides an agent for prophylaxis or treatment of inflammatory bowel diseases, which comprises as an active ingredient sulfodehydroabietic acid (chemical name: (+)-(1R,4aS,10aR)-1,2,3,4,4a,9,10,10a-octadehydro-1,4a-dimethyl-7-(1-methylethyl)-6-sulfo-1-phenanthrenecarboxylic acid) of the following formula (I):

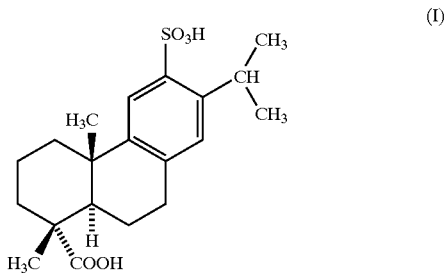

or a pharmaceutically acceptable salt thereof.

The present invention also relates to a use of said sulfodehydroabietic acid (I) or a pharmaceutically acceptable salt thereof in preparation of an agent for prophylaxis or treatment of inflammatory bowel diseases.

Moreover, the present invention provides a method for prophylaxis or treatment of inflammatory bowel diseases which comprises administering said sulfodehydroabietic acid (I) or a pharmaceutically acceptable salt thereof orally or parenterally to a patient being suffering from an inflammatory bowel disease.

BEST MODE FOR CARRYING OUT THE INVENTION

The active ingredient of the present agent for prophylaxis or treatment of inflammatory bowel diseases, sulfodehydroabietic acid of the formula (I) or a pharmaceutically acceptable salt thereof, is a known compound, and can be prepared, for example, by the methods disclosed in JP-A-58-77814, JP-A-63-165361, JP-A-2-167258, or by a modified method thereof.

The pharmaceutically acceptable salt of sulfodehydroabietic acid of the formula (I) includes, for example, a salt with an alkali metal (e.g., sodium, lithium, potassium, etc.), a salt with an alkaline earth metal (e.g., magnesium, calcium, etc.), and a salt with a metal such as aluminum. Among them, the preferable salt is a sodium salt of sulfodehydroabietic acid, especially a monosodium salt or a disodium salt thereof, and the most preferable salt is sulfodehydroabietic acid monosodium salt. Sulfodehydroabietic acid monosodium salt is more advantageous than disodium salt thereof as being less hygroscopic and being more stable (JP-A-63-165361). Besides, a pharmaceutically acceptable salt of sulfodehydroabietic acid may exist as well in the form of a hydrate thereof, and the hydrate of sulfodehydroabietic acid monosodium salt may be, for example, pentahydrate thereof, i.e., sulfodehydroabietic acid monosodium salt pentahydrate. The monosodium salt pentahydrate of sulfodehydroabietic acid of the formula (I) (chemical name: (+)-(1R,4aS,10aR)-1,2,3,4,4a,9,10,10a-octahydro-1,4a-dimethyl-7-(1- methylethyl)-6-sulfo-1-phenanthrenecarboxylic acid 6-sodium salt pentahydrate) has been known as Ecabet sodium.

According to the study of the present inventors, sulfodehydroabietic acid (I) or a pharmaceutically acceptable salt thereof of the active ingredient is hardly absorbed at the gut, and when it is administered orally, it can efficiently reach to the inferior gut and can adhere to the mucosa of the lesion site, and exhibit the pharmacological effects thereof so that the efficacy thereof is extremely excellent. In addition, sulfodehydroabietic acid (I) or a pharmaceutically acceptable salt thereof of the active ingredient shows few side effects, and the safety thereof is extremely high.

The agent for prophylaxis or treatment of inflammatory bowel diseases of the present invention is effective on the lesion of the intestine (including fistula) in Crohn's disease, the lesion of the intestine in Behçet's diseases, ulcerative colitis, hemorrhagic rectal ulcer, ileum pouchitis, etc.

Besides, since sulfodehydroabietic acid (I) or a pharmaceutically acceptable salt thereof of the active ingredient of the present invention can cure the lesion of the gut without causing a stenosis, it may also be useful in the prophylaxis of the stenosis of the gut, especially in the prophylaxis of the stenosis of the intestine accompanying with inflammatory bowel diseases. When surgically treating a patient of an inflammatory bowel disease, an artificial anus may be constructed, but in said patient, such an inflammation may occasionally spread to the periphery of the artificial anus. The sulfodehydroabietic acid (I) or a pharmaceutically acceptable salt thereof of the active ingredient of the present invention is also effective in the inflammation of artificial anus periphery.

The sulfodehydroabietic acid (I) or a pharmaceutically acceptable salt thereof of the active ingredient of the present invention may be administered either orally or rectally, and further can be administered directly into the intestine through an artificial anus in a patient having one, or can directly be applied in the inflammation of the periphery of ane artificial anus.

The present agent for prophylaxis or treatment of inflammatory bowel diseases can be used in the form of oral preparation, intra-intestinal infusion preparation, suppository preparation, or external preparation, which should be selected according to the administration routes. Oral preparation may be solid preparations such as tablets, capsules, powders, granules, or liquid preparation such as solutions, suspension, etc. A preparation being suitable for oral administration may contain a pharmaceutically acceptable carrier or excipient. A pharmaceutically acceptable carrier or excipient being suitable for a solid preparation such as tablets or capsules may be, for example, binders (e.g., acacia, gelatin, dextrin, hydroxypropylcellulose, methylcellulose, polyvinylpyrrolidone), diluents (e.g., lactose, sucrose, mannitol, corn starch, potato starch, calcium phosphate, calcium citrate, crystalline cellulose), lubricants (e.g., magnesium stearate, calcium stearate, stearic acid, talc, anhydrous silicic acid), disintegrants (e.g., corn starch, potato starch, carboxymethylcellulose, carboxymethylcellulose calcium, alginic acid), and wetting agents (e.g., sodium laurylsulfate). A pharmaceutically acceptable carrier or excipient being suitable for a liquid preparation such as solutions or suspensions may be, for example, aqueous vehicles (e.g., water), suspending agents (e.g., acacia, gelatin, methyl cellulose, carboxymethylcellulose sodium, hydroxymethylcellulose, aluminum stearate gel), surfactants (e.g., lecithin, sorbitan monooleate, glycerin monostearate), and non-aqueous vehicles (e.g., glycerin, propylene glycol, vegetable oil). Moreover, liquid preparations may contain preservatives (e.g., p-hydroxybenzoic acid methyl ester, p-hydroxybenzoic acid propyl ester), flavors, and/or coloring agents.

The intra-intestinal infusion (enema) preparation may be in the form of aqueous solution or suspension using the above-mentioned aqueous vehicles or suspending agents. If necessary, the intra-intestinal infusion preparation may be in the form of sol or gel preparation using a thickening agent such as polyacrylic acid, gelatin, etc.

The suppository may be ones which are prepared by mixing the active ingredient of the formula (I) or a pharmaceutically acceptable salt thereof with a commercially available oily base such as Witepsole, etc., or a water-soluble base such as macrogol, glycerogelatin, etc. by a conventional method, and may be in the form of capsule-type suppository, tablet-type suppository, or ointment-type suppository.

The external preparation may include external powder preparations, ointments, creams, etc.

In the present specification, the term "prophylaxis or treatment" comprises the improvement of symptoms, the prevention of exacerbation, the maintainance of remission, the prevention of recrudescence, the prevention of the stenosis of the gut, and more comprises the prevention of recrudescence after surgical operation and the prevention of the stenosis of the operated region.

The dose of the compound (I) or a pharmaceutically acceptable salt thereof of the active ingredient of the present agent may vary according to the administration route, age, weight or conditions of a patient, or severity of the disease to be cured, but the daily dose thereof for an adult is usually in the range of about 10 mg to 300 mg/kg, preferably in the range of about 20 mg to 300 mg/kg, especially in the range of 50 mg /kg to 200 mg/kg.

In the present specification, the inflammatory bowel diseases mean not only inflammatory bowel disease in a strict sense such as Crohn's disease, ulcerative colitis, but also inflammatory bowel disease in a broad sense including the lesion of the intenstine accompanying with Behçet's disease, hemorrhagic rectal ulcer, ileum pouchitis, intestinal tuberculosis, ischemic enteritis, drug-induced colitis, radiation enteritis, infective enteritis, etc.

EXAMPLES

The present agent and its efficacy will be illustrated in more detail by the following Experiments and Preparations.

Experiment 1
Prophylactic or Therapeutic Effect on Acetic Acid-induced Intestinal Injury:

Sulfodehydroabietic acid monosodium salt pentachloride (hereinafter referred to as Ecabet sodium) of the active ingredient of the present invention was previously administered to Fischer rats, and the prophylactic or therapeutic effect thereof on intestinal mucosal injury induced by intra-intestinal infusion of acetic acid was studied.

Namely, granules containing Ecabet sodium (0.5 g, trade name: Gastrome granule, containing 1.0 g of Ecabet sodium per 1.5 g, hereinafter simply referred to as Ecabet sodium-containing granules) were suspended in a physiological saline, and the mixture was injected intra-rectally to Fischer rats. One hour thereafter, a 25% acetic acid solution was intra-rectally injected to the rats. Two hours after the administration of acetic acid, the intestine was excised from the rats, and the histopathological changes in the surface of the intestinal inner wall was observed visually and with a microscope, and the injury of the intestinal mucosa was evaluated both macroscopically and histologically. In the control group, the same procedures were repeated except for that a physiological saline was administered instead of a suspension of Ecabet sodium-containing granules in a physiological saline.

In the results, the intestinal mucosal injury induced by acetic acid was broadly observed in the physiological saline-treated rats while the intestinal mucosal injury was hardly observed in the rats treated with Ecabet sodium of the active ingredient of the present invention, by which it is proved that the active compound (I) of the present invention was useful as an agent for prophylaxis or treatment of inflammatory bowel diseases. In addition, the degree of the intestine mucosal injury between the physiological saline-treated group and the Ecabet sodium-treated group was scored and compared according to the criteria as mentioned below, which was based on the method for Classification and Evaluation of Macpherson, B. R. et al., Digestion, 17, p. 135–150 (1978). The data is indicated in Table 1.

TABLE 1

|  | Degree of Macroscopic Injury | Degree of Histological Injury |
| --- | --- | --- |
| Physiological saline-treated group (Control) | 11.6 ± 0.2 | 10 ± 0.3 |
| Ecabet sodium-treated group | 1.3 ± 0.2 | 2.3 ± 0.4 |

Note: Each value of the score in the above Table 1 is mean ± s.e. of the sum of the scores (0–3) of each item according to the following Score Criteria (1) and (2).

(Score)

(1) Scoring criteria of degree of macroscopic injury:

(i) Visibility of the blood vessel on the mucosa:

| Good | 0 |
| --- | --- |
| Medium degree | 1 |
| (the visible area is more than half of the whole area) | |
| Bad | 2 |
| (the visible area is less than half of the whole area) | |
| Nil | 3 |

(ii) Erythema:

| Nil | 0 |
| --- | --- |
| Linear | 1 |
| Patch | 2 |
| Diffuse | 3 |

(iii) Bleeding:

| Nil | 0 |
| --- | --- |
| Petechial | 1 |
| Patch | 2 |
| Multiple | 3 |

(iv) Erosion/ulcer:

| Nil | 0 |
| --- | --- |
| Small (less than 1 mm × 1 mm) | 1 |
| Medium (less than 5 mm × 5 mm) | 2 |
| Large (5 mm × 5 mm or more) or multiple | 3 |

(2) Scoring criteria of degree of histological injury:

(i) Area of Injury:

| Nil | 0 |
| --- | --- |
| Webbed | 1 |
| Restricted to the basal or terminus region | 2 |
| Diffuse | 3 |

TABLE 1-continued (ii) Edema:

| Nil | 0 |
| --- | --- |
| Low-grade | 1 |
| Medium-grade | 2 |
| High-degree | 3 |

(iii) Bleeding:

| Nil | 0 |
| --- | --- |
| Webbed | 1 |
| Restricted to the basal or terminus region | 2 |
| Diffuse | 3 |

(iv) Erosion/ulcer:

| Nil | 0 |
| --- | --- |
| Upper layer of mucosa | 1 |
| Lower layer of mucosa | 2 |
| Ulcerated | 3 |

Experiment 2

Effect on TNBS-induced Enteritis:

Ecabet sodium of the active ingredient of the present invention was administered to Fischer rats to which TNBS was previously intra-intestinally injected to induce chronic enteritis, and further acetic acid was administered to the rats. Prophylactic or therapeutic effect of Ecabet sodium on the mucosal injury of the intestine induced by acetic acid was studied.

Namely, a solution of TNBS (2,4,6-trinitrobenzenesulfonic acid) in 50% ethanol was injected intra-intestinally to Fischer rats at a dose of 50 mg per 1 kg of the body weight to give the TNBS-induced enteritis. Three weeks thereafter, Ecabet sodium-containing granules (0.5 g) was suspended in a physiological saline, and the mixture was administered intra-rectally to the rats. Thirty minutes thereafter, a 25% acetic acid solution was intra-rectally injected to the rats, and two hours after the acetic acid administration, the intestine was excised from the rats, and the intestinal mucosal injury thereof was scored and evaluated both macroscopically and histologically in the same manner as in Experiment 1 according to the Macpherson's method for Classification and Evaluation. In the control group, the same procedures were repeated except for that a physiological saline was administered instead of a suspension of Ecabet sodium-containing granules in a physiological saline.

The results are shown in Table 2.

TABLE 2

|  | Degree of Macroscopic Injury | Degree of Histological Injury |
| --- | --- | --- |
| Physiological saline-treated group (Control) | 10 ± 0.4 | 11.3 ± 0.5 |
| Ecabet sodium-treated group | 3.9 ± 0.3* | 4.6 ± 0.4* |

*P < 0.05 (against Physiological saline-treated group)

As shown in Table 2, the intestinal mucosal injury observed in the physiological saline-treated rats was effectively inhibited in the Ecabet sodium-treated rats, by which it is proved that the active compound (I) of the present invention is useful as an agent for prophylaxis or treatment of inflammatory bowel diseases.

Experiment 3
Clinical Effects in a Patient of Behçet's Disease:
1) Prehistory Prior to the Administration of the Present Agent:

The patient was a female of 26 years old, whose illness had been diagnosed as intestinal Behçet's disease accompanying with the multiple ulcerative lesion at the small intestine, and who had been medically treated (i.e., administration of a steroid, etc.). Then, the patient was operated surgically twice to excise the intestine on account of massive melena and regional peritonitis but the lesion of the remaining intestine was exacerbated, and further ileus, melena, and peritonitis symptoms caused by anastomotic recrudescence appeared. In order to excise the injured intestine, the abdomen of the patient was incised, but the injured area was so large that the intestine could not be excised, so that a loop ileal artificial anus was installed for administration of Ecabet sodium.

2) Effects of the Administration of the Present Agent:

Ecabet sodium was administered to the patient mentioned above. That is, Ecabet sodium-containing granules (1.5 g) were orally administered twice a day. Further, said granules (1.5 g) were pulverized in a mortar, suspended in water, and the resultant was directly administered into the intestine through the artificial anus twice a day. After the administration of Ecabet sodium, the pain and the melena disappeared in a several days. Moreover, the ulcerative lesion was remarkably improved in the endoscopic finding at 2 weeks after the start of the administration, by which it was confirmed that the lesion was almost cured. Even 7 months after the start of the administration, the recrudescence has not been observed.

Experiment 4
Clinical Effects in a Patient of Crohn's Disease:
1) Prehistory Prior to the Administration of the Present Agent:

The patient was a female of 21 years old, whose illness was diagnosed from the pathological data as large and small intestine Crohn's disease. The exacerbation and the remission were mutually repeated, and the patient was treated with a conventional medicine, but the exacerbation of the anal lesion and the bleeding at the intestine could not be controlled. Although a surgical excision of the lesion was considered, the area of the lesion was so large that it could not be excised, and therefore, a loop ileal artificial anus was installed for administration of Ecabet sodium.

2) Effects of the Administration of the Present Agent:

Ecabet sodium was administered to the patient mentioned above, That is, Ecabet sodium-containing granules (1.5 g) were pulverized in a mortar, suspended in water, and the resultant was directly administered into the intestine through the artificial anus once a day. After the administration, the patient was doing well, and the exacerbation of the condition was not observed even after one year lapsed from the start of the administration.

When the intestinal tissue of the lesion was observed by an endoscope, the injury of the intestinal mucosa which was observed prior to the administration disappeared one year after the start of the administration.

Experiment 5
Clinical Effects in Ulcerative Colitis: 1) Prehistory Prior to the Administration of the Present Agent:

The patient was a female of 49 years old, whose illness was diagnosed as left-sided colon ulcerative colitis. The patient was medicated with mesalazine and a steroid, and treated with leukocytapheresis, but the rectal lesion was remained, and the symptoms were not improved any further. The inflammation was scored as Matts Grade 3 (Quarterly Journal of Medicine, New Series, No. 120, October 1961), and it was so frail that it bled when the endoscopic examination was carried out.

2) Effects of the Administration of the Present Agent:

Ecabet sodium was administered to the patient mentioned above. That is, Ecabet sodium-containing granules (1.5 g) were pulverized in a mortar, suspended in a physiological saline (20 ml), and the resultant was rectally administered through the anus twice a day. After the administration, the inflammation was remitted to Matts Grade 2, and the inflammation area was decreased. That is, when the intestine tissue at the lesion was observed by an endoscope, the inflammation thereof was remarkably improved at 11 days after the start of the Ecabet sodium administration, by which the excellent effect of Ecabet sodium was confirmed. In addition, even 5 months after the start of the administration, the recrudescence was not observed.

Experiment 6
Clinical Effects in Ulcerative Colitis:
1) Prehistory Prior to the Administration of the Present Agent:

The patient was a male of 27 years old, whose illness was diagnosed as left-sided colon ulcerative colitis. The patient was medicated with mesalazine, predonine and a steroid, by which the inflammation was controlled to a degree of disseminated ulcer at the rectum, but further improvement was not obtained.

2) Effects of the Administration of the Present Agent:

Ecabet sodium was administered to the patient mentioned above. That is, Ecabet sodium-containing granules (1.5 g) were pulverized in a mortar, suspended in a physiological saline (20 ml), and the resultant was rectally administered through the anus twice a day. After the administration, the ulcer was improved into a red scar. Namely, when the intestinal tissue of the lesion was observed with an endoscope, the ulcer was turned into a red scar at 18 days after the start of the Ecabet sodium administration. The intractable ulcer can hardly be cured into a red scar, and hence, the remarkable effects of Ecabet sodium are confirmed.

Experiment 7
Clinical Effects in Ulcerative Colitis:
1) Prehistory Prior to the Administration of the Present Agent:

The patient was a female of 58 years old, whose illness was diagnosed as left-sided colon ulcerative colitis. The patient was medicated with salazosulfapyridine and predonine, and treated with leukocytapheresis, but the inflammation condition at the rectum could not be controlled, and the bleeding and the melena lasted.

2) Effects of the Administration of the Present Agent:

Ecabet sodium was administered to the patient mentioned above. That is, Ecabet sodium-containing granules (1.5 g) were pulverized in a mortar, suspended in a physiological saline (20 ml), and the resultant was rectally administered through the anus twice a day. After the administration, the inflammation condition was remarkably improved, and only a slight erythema was remained. Namely, when the intestinal tissue of the lesion was observed by an endoscope, the inflammation almost disappeared at 12 days after the start of the Ecabet sodium administration, and the remarkable improvement of the symptoms was obtained by the administration of Ecabet sodium.

The observations of the lesion after and before the Ecabet sodium administration in the cases of ulcerative colitis of Experiments 5–7 are shown in Table 3.

TABLE 3

|  | Before the administration of Ecabet sodium | After the administration of Ecabet sodium |
| --- | --- | --- |
| Experiment 5 (49 years old female) | Inflammation of Matts Grade 3 | Inflammation of Matts Grade 2 Area of inflammation was reduced |
| Experiment 6 (27 years old male) | Intractable ulcer | Improvement into a red scar |
| Experiment 7 (58 years old female) | Inflammation of mild to moderate | Improvement into a slight erythema |

Experiment 8
Clinical Effects in Acute Hemorrhagic Rectal Ulcer:
1) Prehistory Prior to the Administration of the Present Agent:
The patient was a male of 74 years old, who was hospitalized for treatment of HCV-associated hepatocirrhosis, hepatocellular carcinoma and esophageal varices. After the endoscopic ossification treatment for the esophageal varices was done, an acute hemorrhagic rectal ulcer appeared at whole of the lower rectum. The patient was treated with total parenteral nutrition for 52 days, but the conditions were not improved.
2) Effects of the Administration of the Present Agent:
Ecabet sodium was administered to the patient mentioned above. That is, Ecabet sodium-containing granules (1.5 g) were suspended in water, and the resultant was injected through the anus twice a day for about 1.5 month. The ulcer was cured without any cicatricial stenosis.

Experiment 9
Clinical Effects in Acute Hemorrhagic Rectal Ulcer:
1) Prehistory Prior to the Administration of the Present Agent:
The patient was a female of 72 years old, who was hospitalized for treatment of the right thighbone break. During the treatment thereof, an acute hemorrhagic rectal ulcer occurred at whole of the lower rectum. The patient was treated with total parenteral nutrition, but the conditions were not improved.
2) Effects of the Administration of the Present Agent:
Ecabet sodium was administered to the patient mentioned above. That is, Ecabet sodium-containing granules (1.5 g) were suspended in water, and the resultant was injected through the anus twice a day for about 2.5 months. The ulcer was cured without any cicatricial stenosis.

Experiment 10
Clinical Effects in Acute Hemorrhagic Rectal Ulcer:
1) Prehistory Prior to the Administration of the Present Agent:
The patient was a female of 79 years old, who was hospitalized for treatment of pancreatic cancer. During the treatment, an acute hemorrhagic rectal ulcer appeared at whole of the lower rectum.
2) Effects of the Administration of the Present Agent:
Ecabet sodium was administered to the patient mentioned above. That is, Ecabet sodium-containing granules (1.5 g) were suspended in water, and the resultant was injected through the anus twice a day for about 1 month. The ulcer was cured without any cicatricial stenosis.

Experiment 11
Clinical Effects in Ileum Pouchitis:
1) Prehistory Prior to the Administration of the Present Agent:
The patient was a male of 42 years old. During the postoperative treatment, ileum pouchitis accompanying with acute hemorrhagic ulcer appeared at the ileum pouch which was subjected to ileal pouch/anal anastomosis by the operation for ulcerative colitis.
2) Effects of the Administration of the Present Agent:
Ecabet sodium was administered to the patient mentioned above. That is, Ecabet sodium-containing granules (1.5 g) were suspended in water, and the resultant was injected through the anus twice a day for about 4 months. The ileum pouchitis and the ulcer were cured without any cicatricial stenosis.

Preparation 1

Ecabet sodium (700 g), D-mannitol (252.7 g), sodium chloride (20 g), aspartame (5 g) and magnesium stearate (20 g) were granulated by a wet granulator, and thereto were added L-menthol (0.3 g) and hydrous silicon dioxide (2 g), and the mixture was mixed to give granules.

Preparation 2

To Ecabet sodium (700 g), D-mannitol (255 g), sodium chloride (20 g), aspartame (5 g) and magnesium stearate (20 g) were added water, and the mixture was granulated by a wet granulator to give granules.

Preparation 3

Ecabet sodium (700 g), D-mannitol (175 g), sodium chloride (105 g) and magnesium stearate (20 g) were mixed to give powders.

Preparation 4

Ecabet sodium (700 g), D-mannitol (265.8 g), sodium chloride (7 g), aspartame (5 g) and magnesium stearate (20 g) were granulated by a wet granulator, and thereto were added L-menthol (0.3 g) and hydrous silicon dioxide (2 g), and the mixture was mixed, and compressed with a tableting machine to give tablets.

Preparation 5

Ecabet sodium (700 g), D-mannitol (242.7 g), potassium chloride (30 g), aspartame (5 g) and magnesium stearate (20 g) were granulated with a wet granulator, and thereto were added L-menthol (0.3 g) and hydrous silicon dioxide (2g). The mixture was mixed to give granules.

Preparation 6

The preparation obtained in Preparation 1 was further pulverized in a mortar, and the resultant (3 g) was suspended in water (100 ml) to give an intra-intestinal infusion preparation.

Preparation 7

The preparation obtained in Preparation 2 was further pulverized in a mortar, and the resultant (1.5 g) was suspended in a physiological saline (20 ml) to give an intra-intestinal infusion preparation.

INDUSTRIAL APPLICABILITY

The sulfodehydroabietic acid or a pharmaceutically acceptable salt thereof of the active ingredient of the present invention is useful in the prophylaxis or treatment of inflammatory bowel diseases, which are different in nosogenosis from peptic ulcer or gastritis. In addition, the sulfodehydroabietic acid or a pharmaceutically acceptable salt thereof or a pharmaceutically acceptable salt thereof to a patient suffering from an inflammatory bowel disease.

of the active ingredient of the present invention is hardly absorbed at the gut so that it shows few side effects even by oral administration, and can efficiently adhere to the mucous membrane of the targeted intestine region and depress the inflammation thereof, by which the intestinal lesion can be prevented or cured, so that the prophylaxis or treatment of inflammatory bowel diseases can be achieved with quite efficacy. Further, the agent of the present invention is also effective on intractable inflammatory bowel diseases which cannot be cured by a conventional therapy for inflammatory bowel diseases, and hence, the present agent is quite useful as an agent for prophylaxis or treatment of inflammatory bowel diseases.

What is claimed is:

1. A method for treatment of inflammatory bowel diseases, which comprises administering an effective amount of a compound of the formula (I)

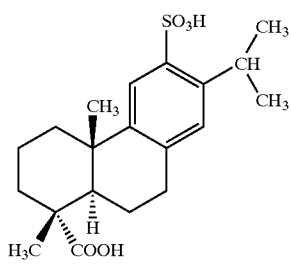
(I)

2. The method for treatment according to claim 1, wherein the pharmaceutically acceptable salt of the compound of the formula (I) is sulfodehydroabietic acid monosodium salt.

3. The method according to claim 1, wherein the inflammatory bowel disease is a disease selected from the group consisting of an intestinal lesion accompanied by Crohn's disease or Behçet's disease, ulcerative colitis, hemorrhagic rectal ulcer and ileum pouchitis.

4. The method according to claim 3, wherein the inflammatory bowel disease is an intestinal lesion accompanied by Crohn's disease.

5. The method according to claim 4, wherein the intestinal lesion accompanied by Crohn's disease is fistula.

6. The method according to claim 3, wherein the inflammatory bowel disease is an intestinal lesion accompanied by Behçet's disease.

* * * * *